United States Patent
Noguchi et al.

(10) Patent No.: US 8,221,308 B2
(45) Date of Patent: Jul. 17, 2012

(54) ENDOSCOPE APPARATUS WITH ADVANCEMENT/RETREAT DETECTION MEANS

(75) Inventors: Toshiaki Noguchi, Tachikawa (JP);
Akira Taniguchi, Fuchu (JP);
Masanobu Koitabashi, Hachioji (JP);
Kouji Nakamoto, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1228 days.

(21) Appl. No.: 11/970,193

(22) Filed: Jan. 7, 2008

(65) Prior Publication Data

US 2008/0146875 A1   Jun. 19, 2008

Related U.S. Application Data

(63) Continuation of application No. PCT/JP2006/313506, filed on Jul. 6, 2006.

(30) Foreign Application Priority Data

Jul. 8, 2005   (JP) ................................. 2005-200359

(51) Int. Cl.
*A61B 1/00* (2006.01)
(52) U.S. Cl. ........................ 600/117; 600/114
(58) Field of Classification Search .................. 600/114, 600/117, 118, 102, 106, 131
See application file for complete search history.

(56) References Cited

U.S. PATENT DOCUMENTS

| | | | |
|---|---|---|---|
| 5,116,317 A * | 5/1992 | Carson et al. ............ 604/102.01 |
| 5,191,373 A * | 3/1993 | Nakano ........................... 396/287 |
| 5,431,645 A * | 7/1995 | Smith et al. ....................... 606/1 |
| 5,623,582 A * | 4/1997 | Rosenberg ....................... 700/264 |
| 5,627,584 A * | 5/1997 | Nishikori et al. ................ 348/72 |
| 5,728,044 A * | 3/1998 | Shan .............................. 600/145 |
| 5,957,833 A * | 9/1999 | Shan .............................. 600/117 |
| 6,038,488 A * | 3/2000 | Barnes et al. .................. 700/161 |
| 6,595,315 B1 * | 7/2003 | Fujimoto et al. .............. 181/124 |
| 6,726,675 B1 * | 4/2004 | Beyar ............................. 604/510 |
| 6,817,973 B2 * | 11/2004 | Merril et al. ................... 600/118 |
| 6,981,945 B1 * | 1/2006 | Sarvazyan et al. ............. 600/131 |
| 7,819,799 B2 * | 10/2010 | Merril et al. ................... 600/118 |
| 2001/0016804 A1 * | 8/2001 | Cunningham et al. ............ 703/7 |
| 2003/0208103 A1 * | 11/2003 | Sonnenschein et al. ....... 600/117 |

(Continued)

FOREIGN PATENT DOCUMENTS

EP          1 543 765 A1    6/2005

(Continued)

OTHER PUBLICATIONS

Appleyard et al., "The measurement of forces exerted during colonoscopy", Gastrointestinal Endoscopy, Elsevier, NL, vol. 52, No. 2, Aug. 1, 2000, pp. 237-240, XP004853683.

(Continued)

*Primary Examiner* — John P Leubecker
(74) *Attorney, Agent, or Firm* — Scully, Scott, Murphy & Presser, P.C.

(57) ABSTRACT

A direction of movement, an insertion amount and an insertion force amount at a time when an insertion section of an endoscope is inserted in a large intestine, which is an object of an inspection, are detected by detection unit. The direction of movement, the insertion amount and the insertion force amount of the insertion section are displayed on a display device which is separably disposed. Thereby, a high-precision insertion operation can simply and easily be realized, and a handling operability is improved.

10 Claims, 6 Drawing Sheets

U.S. PATENT DOCUMENTS

| | | | |
|---|---|---|---|
| 2004/0176683 A1* | 9/2004 | Whitin et al. | 600/424 |
| 2006/0009679 A1* | 1/2006 | Ito et al. | 600/117 |
| 2006/0161043 A1* | 7/2006 | Neumann et al. | 600/114 |
| 2007/0249901 A1* | 10/2007 | Ohline et al. | 600/117 |
| 2008/0039685 A1* | 2/2008 | Komiya et al. | 600/106 |

FOREIGN PATENT DOCUMENTS

| | | |
|---|---|---|
| JP | 61-203934 | 9/1986 |
| JP | 6-54795 | 3/1994 |
| JP | 6-304127 | 11/1994 |
| JP | 2000-107123 | 4/2000 |
| WO | WO 99/45994 | 9/1999 |

OTHER PUBLICATIONS

Mosse et al., "Device for Measuring the Forces Exerted on the Shaft of an Endoscope During Colonoscopy", Medical and Biological Engineering and Computing, Springer, Heildelberg, DE, vol. 36, No. 2, Mar. 1, 1998, pp. 186-190, XP000739385.

Zaaijer et al., "Reliability of polymerase chain reaction for detection of hepatitis C virus", Lancet, vol. 341, No. 8847, Mar. 20, 1993, pp. 719-722, XP002551109.

Extended Supplementary European Search Report dated Oct. 29, 2009.

* cited by examiner

ENDOSCOPE APPARATUS WITH ADVANCEMENT/RETREAT DETECTION MEANS

CROSS-REFERENCE TO RELATED APPLICATIONS

This is a Continuation Application of PCT Application No. PCT/JP2006/313506, filed Jul. 6, 2006, which was published under PCT Article 21(2) in Japanese.

This application is based upon and claims the benefit of priority from prior Japanese Patent Application No. 2005-200359, filed Jul. 8, 2005, the entire contents of which are incorporated herein by reference.

BACKGROUND OF THE INVENTION

1. Field of the Invention

The present invention relates to an endoscope apparatus which is inserted in an object of an inspection, such as a living body organ, and is used to observe the inside of the object and to perform a therapeutic treatment of a part which undergoes an operation.

2. Description of the Related Art

In general, an endoscope apparatus includes an elongated soft insertion section which extends from an endoscope body. The insertion section is inserted into a lumen of an object of an inspection, such as an organ or a body cavity of a patient, and a diseased part is observed. Alternatively, a therapeutic device is used in combination with the insertion section that is inserted in the lumen of the object of an inspection. Thus, the endoscope apparatus is used for therapeutic treatment of a diseased part within the body, such as resection of a mucous membrane, without ventrotomy as in a surgical operation.

In this endoscope apparatus, a bend section which is capable of performing a bend operation is provided at a distal end portion of the insertion section, and a soft distal end portion is formed on the bend section. Thereby, insertion of the insertion section into the lumen of the object of an inspection, for example, an organ, is facilitated, and the inside of the object of the inspection can be observed over a wide range (see, e.g. Jpn. Pat. Appln. KOKAI Publications Nos. H6-54795 and 2000-107123).

In the meantime, in the endoscope apparatus, a high-level insertion operation is required at the time of a work of inserting the insertion section into a desired position within the lumen of the object of inspection. For example, the insertion section needs to be advanced/retreated in the direction of insertion, while combining, for example, an operation of bending the distal end portion of the insertion section and an operation of turning the insertion section about the axis thereof.

In particular, in a case of performing a work of inserting the insertion section of the endoscope into the large intestine, the insertion operation of the insertion section is difficult. In this case, the large intestine itself has a complex shape, and the shape of the large intestine varies from patient to patient. Thus, at the time of performing the work of inserting the insertion section of the endoscope, precision is required in the work of adjusting, for instance, an insertion amount and an insertion force amount of the insertion section of the endoscope. As a result, in the case of giving instruction to less experienced surgeons as to how to insert the insertion section of the endoscope, such a method has conventionally been adopted that the actual insertion operation of the insertion section of the endoscope is observed under the tuition of well experienced doctors, and the know-how of, e.g. the adjustment of the insertion amount and insertion force amount is learned.

BRIEF SUMMARY OF THE INVENTION

According to a first aspect of the present invention, there is provided an endoscope apparatus comprising: an endoscope having an insertion section which is inserted into a lumen that is an object of an inspection; detection means, in which the insertion section is advancibly/retreatably inserted, for detecting a direction of movement, an insertion amount and an insertion force amount of the insertion section in relation to the object of the inspection, which occur in association with an advancement/retreat operation of the insertion section; and display means for displaying the direction of movement, the insertion amount and the insertion force amount of the insertion section, which are detected by the detection means.

According to the above-described structure, when the insertion section is inserted in the object of inspection, the direction of insertion, the insertion amount and the insertion force amount of the insertion section are detected by the detection means, and the direction of insertion, the insertion amount and the insertion force amount are displayed on the display means. Thereby, the insertion state is recognized on the basis of the display. Accordingly, persons around, including the operator, can perform a subsequent insertion operation by recognizing the present state of the insertion section of the endoscope. Therefore, stable, high-precision insertion operations can easily be performed.

Preferably, the display means is disposed separately from the endoscope.

Preferably, the display means includes display sections which display a maximum insertion amount, a maximum insertion force amount and a minimum insertion force amount of the insertion section.

Preferably, the display means includes display sections which display presence/absence of insertion stop, an excessive insertion amount and an excessive insertion force amount of the insertion section.

Preferably, the display means includes: a present-state display section which displays the direction of movement, the insertion amount and the insertion force amount of the insertion section, which are detected by the detection means; a cumulative display section which displays a maximum insertion amount, a maximum insertion force amount and a minimum insertion force amount of the insertion section; and a condition display section which displays presence/absence of insertion stop, an excessive insertion amount and an excessive insertion force amount of the insertion section.

Preferably, the display means includes a display-object change-over switch which changes an object of display.

Preferably, the detection means includes: a guide roller which guides the insertion section in a direction of advancement/retreat; an insertion amount detection section which detects the insertion amount of the insertion section; and an insertion force amount detection section which detects the insertion force amount of the insertion section.

Preferably, the detection means includes an insertion operation detection unit, the insertion operation detection unit includes a unit body which includes: a substantially cylindrical endoscope guide cylindrical member having a distal end portion and a proximal end portion, an insertion hole for guiding insertion of the insertion section being formed by an inner cavity of the guide cylindrical member; and an insertion force amount detection section which is provided on the proximal end portion of the guide cylindrical member, and the insertion force amount detection section includes: a plurality of guide rollers disposed around the insertion hole; base members which support the guide rollers; rotational plates each having one end portion supported on the base member so as to be rotatable about a rotational shaft, and having the other end portion to which the guide roller is rotatably supported so as to be rotatable about a rotational shaft; a pressure sensor which is disposed to be opposed to the rotational plate on a locus of rotation of the rotational plate, and detects a pressure due to a contact/separation operation of the rotational plate in interlock with rotation of the rotational plate; and a control circuit which detects an insertion force amount due to an insertion operation of the insertion section, on the basis of a detection signal from the pressure sensor.

Preferably, the insertion section has a plurality of magnetic portions which are formed in annular shapes on an outer periphery thereof, the magnetic portions being juxtaposed at predetermined intervals along an axial direction of the insertion section, the guide cylindrical member includes an insertion amount detection section at an intermediate part thereof, the insertion amount detection section detects the magnetic portions when the insertion section is inserted in the insertion hole and the insertion section passes by an inside of the insertion amount detection section, and the control circuit detects the direction of movement and the insertion amount of the insertion section on the basis of a detection signal from the insertion amount detection section.

Preferably, the guide roller has, on a side surface thereof, a plurality of magnetic portions juxtaposed at predetermined intervals along a circumferential direction of a circle centering on the rotational shaft, the base member is provided with an insertion amount detection section, the insertion amount detection section detects the magnetic portions on the side surface of the guide roller in accordance with a rotational operation of the guide roller, which occurs due to movement of the insertion section, and the control circuit detects a rotational angle of the guide roller on the basis of a detection signal from the insertion amount detection section, and detects the direction of movement and the insertion amount of the insertion section.

Preferably, the insertion amount detection section is composed of a Hall element.

The present invention can provide an endoscope apparatus which can realize a simple, easy, high-precision insertion operation, and can improve handling operability.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
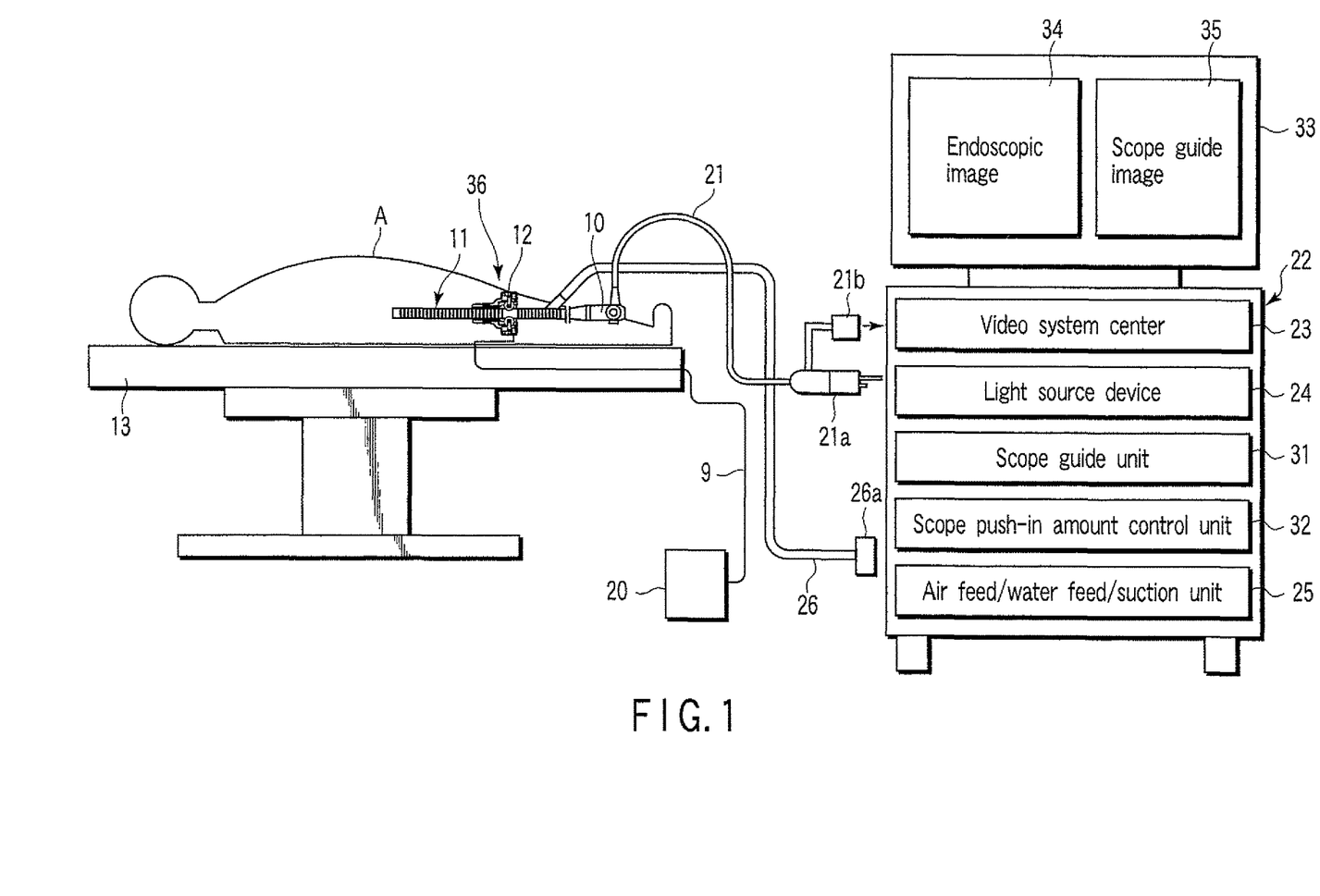
FIG. 1 schematically shows the structure of the entire system of an endoscope apparatus according to a first embodiment of the present invention.

A first embodiment of the present invention will now be described with reference to FIG. 1 to FIG. 5. FIG. 1 schematically shows the structure of the entire system of an endoscope apparatus according to the first embodiment of the invention. The system of the endoscope apparatus includes an electronic endoscope 1 and a data processing device 22.

The electronic endoscope 1 includes an elongated soft insertion section 11 and an operation section 10 which is coupled to a proximal end portion of the insertion section 11. The insertion section 11 is inserted in a lumen of an object of an inspection, for example, in a body cavity of a patient A lying on a bed 13. The insertion section 11 includes an elongated flexible tube section, a bend section which is coupled to a distal end of the flexible tube section, and a distal-end hard section which is coupled to a distal end of the bend section. The operation section 10 is provided with a bend operation device, operation buttons for operations such as air feed, water feed and suction, and various operation buttons for imaging of the endoscope 1, which are not shown.

Figure 5:
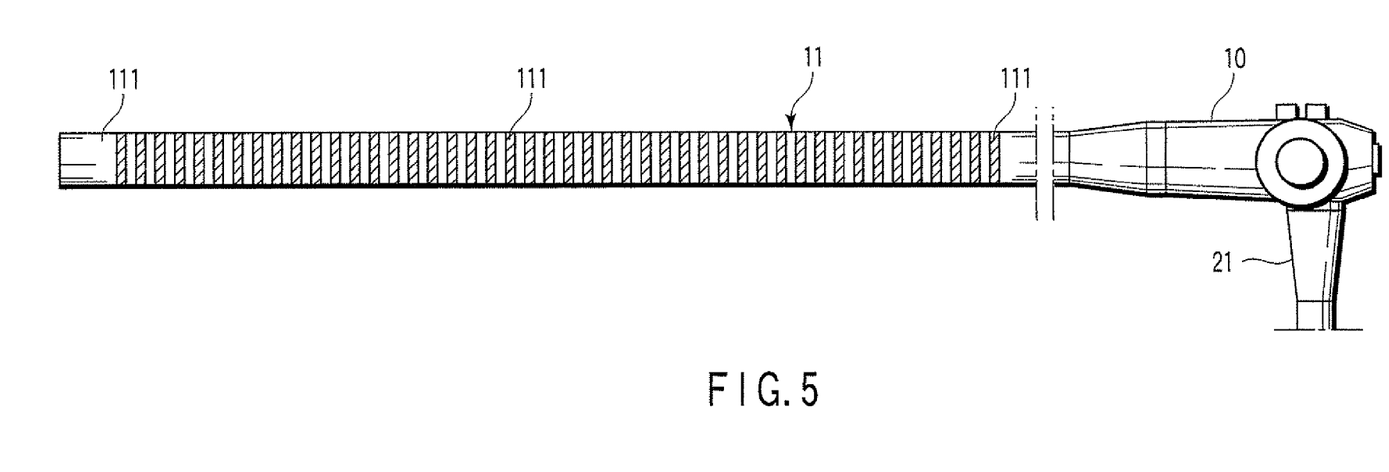
FIG. 5 is a side view which schematically shows the structure of the insertion section of the endoscope apparatus according to the first embodiment.

Further, as shown in FIG. 5, as regards the insertion section 11 of the endoscope 1, a plurality of magnetic portions 111, which are formed in an annular shape around the outer periphery of the insertion section 11, are juxtaposed at predetermined intervals along the axial direction of the insertion section 11. Each magnetic portion 111 is formed in an annular shape by coating a magnetic body with a predetermined width over the outer periphery of the insertion section 11.

The data processing device 22 includes a video system center 23, a light source device 24, an air feed/water feed/suction unit 25, a scope guide unit 31, a scope push-in amount control unit 32, and a monitor 33 which is connected to the video system center 23. The air feed/water feed/suction unit 25 controls air feed, water feed and suction. The scope guide unit 31 includes necessary-part pressing force amount detection. The scope push-in amount control unit 32 detects and controls the push-in amount and push-in pressure of the insertion section 11. Further, the monitor 33 includes a screen 34 which displays an endoscopic image, and a screen 35 which displays a scope guide image.

In the electronic endoscope 1, one end portion of the coupling tube 26, which contains tubes for air feed, water feed and suction, is coupled to a proximal end portion of the insertion section 11. The other end portion of the coupling tube 26 is connected to the air feed/water feed/suction unit 25 of the data processing device 22 via a tube connection section 26a. Air feed, water feed and suction through the tubes for air feed, water feed and suction in the endoscope insertion section 11 are performed from the air feed/water feed/suction unit 25 via the coupling tube 26.

Further, one end portion of a universal cord 21, which contains a light guide fiber and an electric signal line (not shown), is coupled to the operation section 10. The other end portion of the universal cord 21 is provided with an optical connection section 21a and an electrical connection section 21b. The optical connection section 21a is connected to the light source device 24 of the data processing device 22. The electrical connection section 21b is connected to the video system center 23 of the data processing device 22. Illumination light from the light source device 24 is transmitted to the light guide fiber within the operation section 10 and insertion section 11 of the endoscope 1 via the light guide fiber within the universal cord 21. Furthermore, the illumination light, which has been transmitted to the distal end of the light guide fiber, is emitted to the outside via an illumination lens that is disposed in the distal-end hard section.

An observation image of the endoscope 1, which is made incident from an observation lens disposed at the distal-end hard section, is captured by an imaging device such as a CCD. The observation image of the endoscope 1, which is captured by the imaging device, is converted to an electric signal. An output signal from the imaging device is input to the video system center 23 via the electric signal line within the insertion section 11 and operation section 10 of the endoscope 1 and the electric signal line within the universal cord 21. An electric signal, which is processed in the video system center 23, is input to the monitor 33, and the observation image of the endoscope 1 is displayed on the display screen 34 for endoscopic images.

Figure 2:
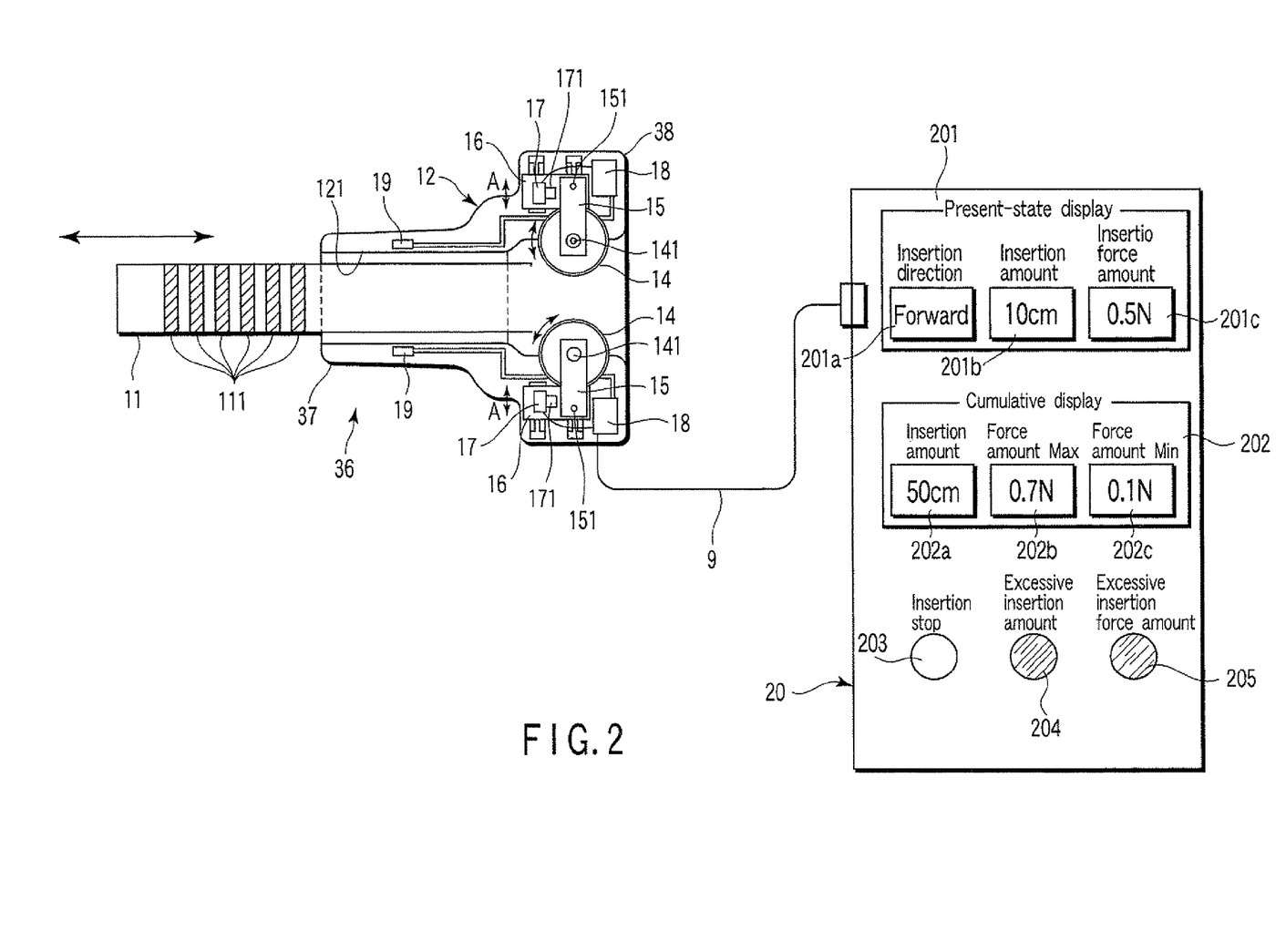
FIG. 2 schematically shows the structures of a main part of an insertion operation detection unit and a display device, which are used in the endoscope apparatus according to the first embodiment.

The system of the endoscope apparatus according to the present embodiment includes an insertion operation detection unit 36 which detects a direction of movement, an insertion amount and an insertion force amount at a time of inserting the insertion section 11 of the endoscope 1 into the large intestine of the patient A, or the object of inspection, and a display device 20 which displays detection data of the direction of movement, insertion amount and insertion force amount of the insertion section 11 of the endoscope 1, which are the detection data of the insertion operation detection unit 36.

As shown in FIG. 2, the insertion operation detection unit 36 is provided with a unit body 12. The unit body 12 is provided with a substantially cylindrical endoscope guide cylindrical member 37. In the endoscope guide cylindrical member 37, an insertion hole 121 in which the insertion section 11 of the endoscope 1 is inserted is formed by the inner cavity of the guide cylindrical member 37. The distal end portion of the endoscope guide cylindrical member 37 is disposed, for example, in the state in which the distal end portion is inserted in the anus of the patient A lying on the bed 13. The insertion of the insertion section 11 of the endoscope 1 is guided by the insertion hole 121 of the endoscope guide cylindrical member 37.

Figure 3:
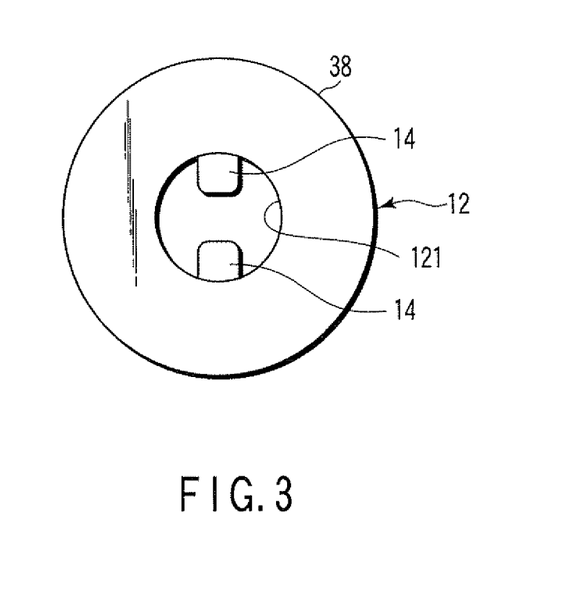
FIG. 3 is a front view showing an endoscope guide cylindrical member, as viewed from the direction of an insertion hole, of the insertion operation detection unit of the endoscope apparatus according to the first embodiment.

A proximal end portion of the endoscope guide cylindrical member 37 is provided with a large-diameter insertion force amount detection section 38. The insertion force amount detection section 38 is provided with a plurality of, for example, a pair of guide rollers 14, and two base members 16 around the insertion hole 121. As shown in FIG. 3, the pair of guide rollers 14 are disposed to be opposed to each other, with the insertion hole 121 being located therebetween. An axis portion of each guide roller 14 is provided with a rotational shaft 141.

One end portion of a rotational plate 15 is supported on each base member 16 so as to be rotatable about a rotational shaft 151. The rotational shaft 141 of the guide roller 14 is rotatably attached to the other end portion of the rotational plate 15.

The two base members 16 are provided to be movable in a direction (indicated by an arrow A in FIG. 2) which is perpendicular to the direction of advancement/retreat of the endoscope insertion section 11 that is inserted in the insertion hole 121 of the unit body 12. The two base members 16 are held in the state in which they are urged by spring members (not shown) toward the insertion hole 121.

Each base member 16 is equipped with a pressure sensor 17 on the locus of rotation of the rotational plate 15. A detection portion 171 of each pressure sensor 17 is disposed to be opposed to a side portion of the rotational plate 15. When the side portion of the rotational plate 15 contacts or separates from the detection portion 171 of each pressure sensor 17 in interlock with the rotation of the rotational plate 15, each pressure sensor 17 detects a pressure corresponding to the contact/separation.

Each pressure sensor 17 is connected to a control circuit 18 which is assembled on each base member 16. A detection signal, which is output from the detection portion 171 of each pressure sensor 17, is input to each control circuit 18. On the basis of the detection signal from the pressure sensor 17, each control circuit 18 detects an insertion force amount corresponding to the insertion operation of the endoscope insertion section 11.

Two insertion amount detection sections 19, for instance, are provided on intermediate portions of the endoscope guide cylindrical member 37. The insertion amount detection sections 19 are disposed to be opposed to each other, with the insertion hole 121 being located therebetween, at positions separated over 180° in the circumferential direction of the insertion hole 121 of the unit body 12.

The insertion amount detection sections 19 are composed of, for example, Hall elements. An output terminal of each insertion amount detection section 19 is connected to each control circuit 18. When the insertion section 11 of the endoscope 1 is inserted into the insertion hole 121 of the insertion operation detection unit 36 and the insertion section 11 of the endoscope 1 passes by the inside of each insertion amount detection section 19, the insertion amount detection sections 19 detect the magnetic portions 111 of the insertion section 11 of the endoscope 1. At this time, a detection signal from each insertion amount detection section 19 is output to the control circuit 18. Based on the detection signal from each insertion amount detection section 19, the control circuit 18 detects the direction of movement and the insertion amount of the insertion section 11 of the endoscope 1.

The control circuits 18 are connected via, e.g. a cable 9, to the display device 20 which displays the state of insertion of the insertion section 11 of the endoscope 1. Thus, the display device 20 is movably disposed so as to be separable from the unit body 12. Accordingly, the display device 20 can be disposed at a proper separate position, such as a position where confirmation can be made by the doctor who operates the insertion section 11 of the endoscope 1, or a position where confirmation can be made by other doctors.

The display device 20 includes, for example, a present-state display section 201, a cumulative display section 202, an insertion stop display section 203, an excessive insertion amount display section 204, an excessive insertion force amount display section 205. The present-state display section 201 includes an insertion direction display section 201a which displays the direction of insertion of the insertion section 11 of the endoscope 1, an insertion amount display section 201b which displays the insertion amount of the insertion section 11, and an insertion force amount display section 201c which displays the insertion force amount of the insertion section 11. The cumulative display section 202 includes a cumulative insertion amount display section 202a which displays the cumulative insertion amount, a force amount Max display section 202b which displays a maximum (Max) insertion force amount, and a force amount Min display section 202c which displays a minimum (Min) insertion force amount.

The insertion stop display section 203 displays presence/absence of insertion stop of the insertion section 11 of the endoscope 1. The excessive insertion amount display section 204 displays presence/absence of an excessive insertion amount. The excessive insertion force amount display section 205 displays presence/absence of an excessive insertion force amount.

The display device 20 may not be connected to the control circuits 18 via the cable 9, and may be connected by, e.g. a wireless configuration. In this case, since there is no restriction to the position of disposition, the usability can be improved.

Next, the operation of the present embodiment having the above-described structure is described. With the above structure, the following process is performed at the time of the work of inserting the insertion section 11 of the endoscope 1 into the large intestine of the patient A. To begin with, the unit body 12 of the insertion operation detection unit 36 is inserted in the anus of the patient A. At this time, the distal end portion of the endoscope guide cylindrical member 37 is disposed, for example, in the state in which the distal end portion is inserted in the anus of the patient A lying on the bed 13.

Then, the insertion section 11 of the endoscope 1 is inserted in the insertion hole 121 of the unit body 12 of the insertion operation detection unit 36. In this state, the insertion section 11 of the endoscope 1 is inserted and guided into the large intestine. At this time, the distal end portion of the insertion section 11 of the endoscope 1, which is inserted in the insertion hole 121 of the unit body 12, is put between the guide rollers 14 under pressure. Thereby, the distal end portion of the insertion section 11 pushes the guide rollers 14 radially outward of the insertion hole 121. Accordingly, the base members 16 move outward.

Figure 4:
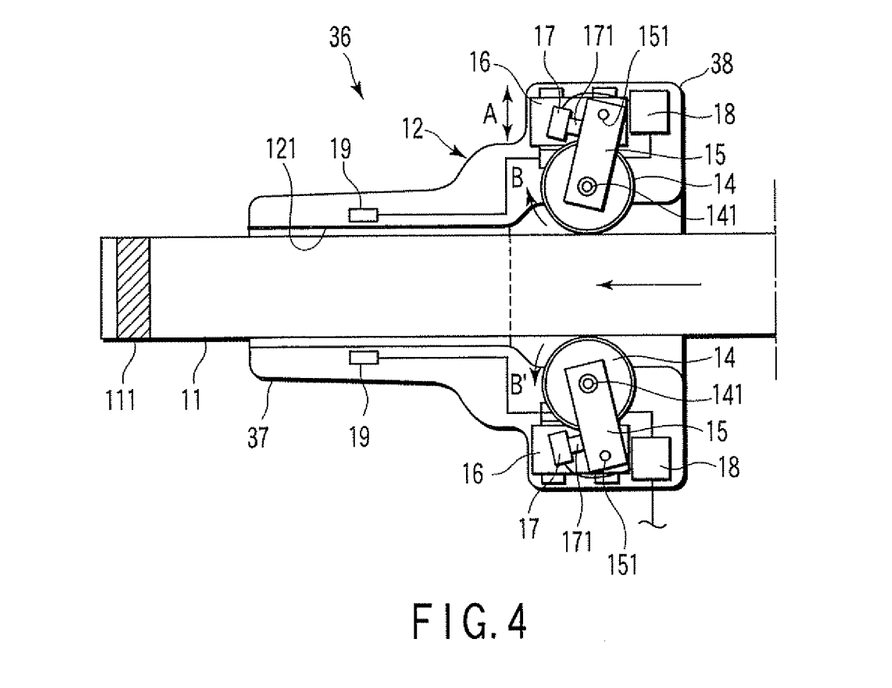
FIG. 4 is a longitudinal cross-sectional view of a main part, illustrating an operation of inserting an insertion section of the endoscope apparatus according to the first embodiment.

At this time, in the state in which the insertion section 11 of the endoscope 1 is clamped between the guide rollers 14, the insertion section 11 of the endoscope 1 is further inserted into the insertion hole 121 and thereby the paired guide rollers 14 are rotated in directions of arrows B in FIG. 4. Specifically, with the forward movement of the insertion section 11 of the endoscope 1, the rotational plate 15 of the upper guide roller 14, in FIG. 4, is rotated clockwise (direction of arrow B) about the rotational shaft 151. Similarly, the rotational plate 15 of the lower guide roller 14, in FIG. 4, is rotated counterclockwise (direction of arrow B') about the rotational shaft 151.

At this time, the distance between the paired guide rollers 14 is widened by the insertion section 11 of the endoscope 1, and the rotational plates 15 are rotated clockwise and counterclockwise, in the Figure, about the rotational shafts 151. Thus, the detection portions 171 of the pressure sensors 17 are pressed by the side portions of the rotational plates 15. Thereby, the pressure sensors 17 detect the rotational forces of the rotational plates 15, and output pressure detection signals to the control circuits 18. Further, On the basis of the pressure detection signals of the pressure sensors 17, the control circuits 18 find an insertion force amount of the endoscope insertion section 11.

When the insertion section 11 of the endoscope 1 is inserted into the insertion hole 121 of the insertion operation detection unit 36 and then the insertion section 11 of the endoscope 1 passes by the inside of each insertion amount detection section 19, the insertion amount detection sections 19 detect the magnetic portions 111 of the insertion section 11 of the endoscope 1. At this time, the insertion amount detection sections 19 detect the magnetic portions 111 of the endoscope insertion section 11 that is moved forward, and outputs detection signals to the control circuits 18.

The control circuits 18 find an insertion amount of the endoscope insertion section 11 on the basis of the detections signals of the insertion amount detection sections 19. Further, the insertion amount information and insertion force amount information are input as output signals from the control circuits 18 to the display device 20. Thereby, the insertion direction, insertion amount and insertion force amount of the insertion section 11 of the endoscope 1 are displayed on the present-state display section 201 of the display device 20. At this time, the insertion direction display section 201a displays the direction of insertion of the insertion section 11 of the endoscope 1, which is input from the control circuits 18, the insertion amount display section 201b displays the insertion amount of the insertion section 11, and the insertion force amount display section 201c displays the insertion force amount of the insertion section 11.

Further, the cumulative display section 202 displays the cumulative insertion amount, the maximum insertion force amount, and the minimum insertion force amount. At this time, the cumulative insertion amount display section 202a displays the cumulative insertion amount. Similarly, the force amount Max display section 202b displays the maximum (Max) insertion force amount, and the force amount Min display section 202c displays the minimum (Min) insertion force amount.

On the basis of the detection signals from the insertion amount detection sections 19 and the pressure detection signals from the pressure sensors 17, the control circuits 18 output to the display device 20 an excessive insertion amount signal and an excessive insertion force amount signal in a state in which the insertion amount and the insertion force amount have reached preset values. In this case, the display device 20 displays the excessive insertion amount state and excessive insertion force amount state, for example, by lighting the excessive insertion amount display section 204 and excessive insertion force amount display section 205.

In addition, if the control circuits 18 determine, on the basis of the detection signals of the insertion amount detection sections 19, that the endoscope insertion section 11 has stopped for a predetermined time, the control circuits 18 output a stop signal to the display device 20. Based on the stop signal, the display device 20 displays the insertion stop state, for example, by lighting the insertion stop display section 203.

The following advantageous effects can be obtained by the above-described structure. Specifically, the above-described endoscope apparatus is provided with the insertion operation detection unit 36 which detects the direction of movement, the insertion amount and the insertion force amount at the time of inserting the insertion section 11 of the endoscope 1 into the large intestine that is the object of inspection. The display device 20, which is separably disposed, is configured to display the direction of movement, insertion amount and insertion force amount of the insertion section 11 of the endoscope 1.

Thereby, when the insertion section 11 of the endoscope 1 is inserted in the large intestine, the insertion state of the insertion section 11 of the endoscope 1 is recognized on the basis of the direction of movement, insertion amount and insertion force amount of the insertion section 11 of the endoscope 1, which are displayed on the display device 20. As a result, persons around, including the person performing the insertion operation, can perform a subsequent insertion operation while recognizing the present state of the insertion section 11 of the endoscope 1. Thus, the stable insertion operation can easily be performed.

In the above-described first embodiment, in the structure for detecting the insertion amount of the insertion section 11 of the endoscope 1, the plural magnetic portions 111 are juxtaposed at predetermined intervals along the axial direction over the outer periphery of the insertion section 11 of the endoscope 1, and the insertion amount detection sections 19 are provided in the unit body 12. The structure, however, is not limited to this. For example, alteration may be made as in a second embodiment of the invention shown in FIG. 6 and FIG. 7, which will be described below.

Figure 6:
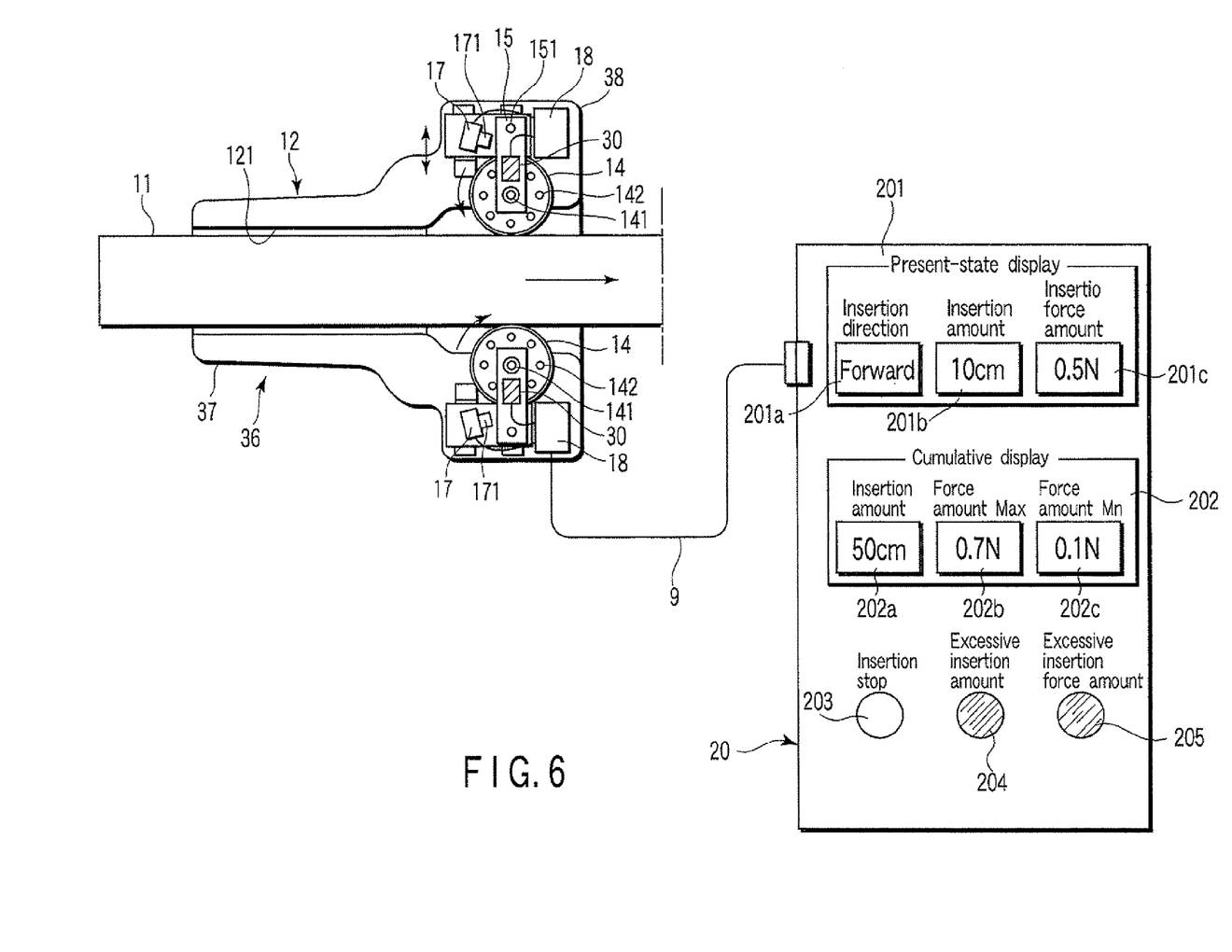
FIG. 6 schematically shows the structures of a main part of an insertion operation detection unit and a display device, which are used in an endoscope apparatus according to a second embodiment of the present invention.
Figure 7:
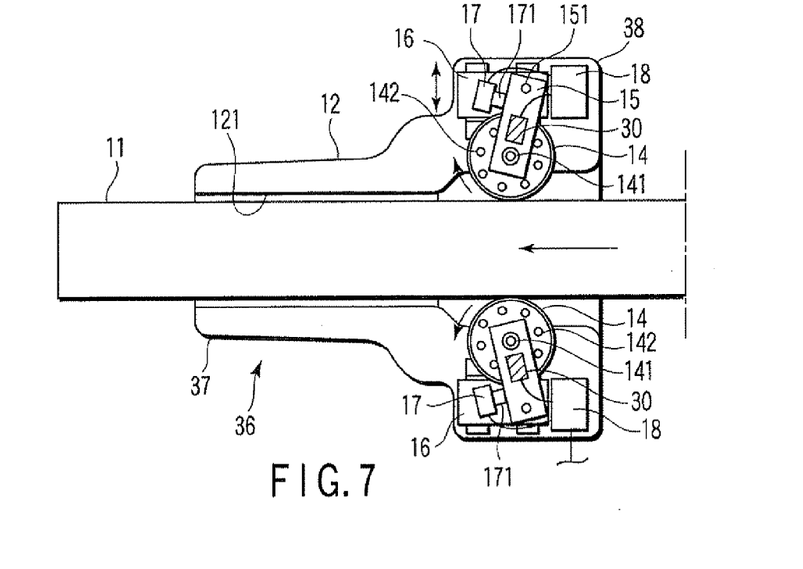
FIG. 7 is a longitudinal cross-sectional view showing, in enlarged scale, a main part in FIG. 6.

FIG. 6 and FIG. 7 show a second embodiment of the present invention. In this embodiment, the structure of the scope push-in amount control unit 32 of the first embodiment (see FIGS. 1 to 5) is altered as described below. In FIG. 6 and FIG. 7, the same parts as in FIG. 1 to FIG. 5 are denoted by like reference numerals, and a description is omitted.

Specifically, in the scope push-in amount control unit 32 of the present embodiment, a plurality of dot-shaped magnetic portions 142, which are formed by coating magnetic bodies, are juxtaposed on side surfaces of the pair of guide rollers 14 at predetermined intervals along the circumferential direction of a circle centering on the rotational shaft 141.

Further, insertion amount detection sections 30, which are composed of, e.g. Hall elements, are provided on the base members 16. Each insertion amount detection section 30 is connected to the associated control circuit 18. The insertion section 11 of the endoscope 1 is inserted in the insertion hole 121 of the insertion operation detection unit 36, and the magnetic portions 142 on the side surfaces of the guide rollers 14 are detected by the insertion amount detection sections 30 in accordance with the rotation of the paired guide rollers 14, which is caused by the movement of the insertion section 11 of the endoscope 1. At this time, the detection signals from the insertion amount detection sections 30 are output to the control circuits 18. On the basis of the detection signals from the insertion amount detection sections 30, the control circuits 18 detect the rotational angle of the guide rollers 14 and detect the direction of movement and the insertion amount of the insertion section 11 of the endoscope 1. Subsequently, as has been described above, the insertion amount information and the insertion force amount information of the insertion section 11 of the endoscope 1, which are output from the control circuits 18, are input to the display device 20. Thereby, the present-state display section 201 of the display device 20 displays the insertion direction, insertion amount and insertion force amount of the insertion section 11 of the endoscope 1.

Accordingly, in the present embodiment, like the first embodiment, when the insertion section 11 of the endoscope 1 is inserted in the large intestine, the insertion state of the insertion section 11 of the endoscope 1 is recognized on the basis of the direction of movement, insertion amount and insertion force amount of the insertion section 11 of the endoscope 1, which are displayed on the display device 20. As a result, persons around, including the person performing the insertion operation, can perform a subsequent insertion operation while recognizing the present state of the insertion section 11 of the endoscope 1. Thus, the stable, high-precision insertion operation can easily be performed.

In the present embodiment, the pressure sensors 17 are disposed on the base members 16 in association with the rotational plates 15 of the guide rollers 14. The pressure sensors 17 detect variations of the rotational forces of the rotational plates 15, which are rotated in accordance with the directions of rotation of the guide rollers 14. Thereby, the insertion force amount of the endoscope insertion section 11 can be detected similarly.

In the first and second embodiments, two guide rollers 14 are provided in the unit body 12, with the insertion hole 121 being located therebetween, and two insertion amount detection sections 19 (30) are provided in the unit body 12 so as to be opposed to each other, with the insertion hole 121 being located therebetween. Thereby, the guiding of movement and detection are performed at two locations on the outer periphery of the insertion section 11 of the endoscope 1. The number of these components, however, is not limited to two, and more components may be disposed. In any case of the structures, the same effective advantages can be expected.

In the first and second embodiments, the unit body 12 of the scope push-in amount control unit 32 is inserted in the anus of the patient A, and the insertion section 11 of the endoscope 1 is inserted into the insertion hole 121 of the unit body 12 and into the large intestine that is the object of inspection. Thereby, the direction of movement, insertion amount and insertion force amount of the insertion section 11 of the endoscope 1 are detected. However, the structure of the unit body 12 is not limited to this. For example, the unit body 12 may be positioned in the vicinity of the part of insertion of the object of inspection, other than the anus of the patient A. Thereby, the same advantageous effects can be expected.

In the structures shown in the above embodiments, the display device 20 is provided with the present-state display section 201, cumulative display section 202, insertion stop display section 203, excessive insertion amount display section 204 and excessive insertion force amount display section 205. However, the structure is not limited to this, and other display sections may be provided.

Figure 8:
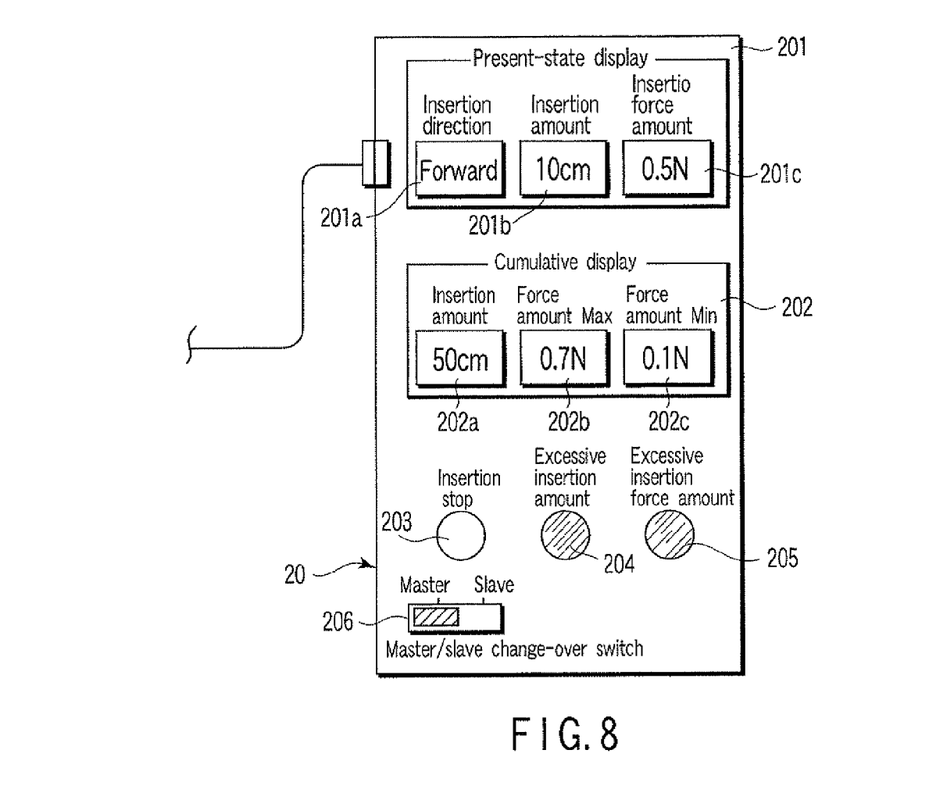
FIG. 8 is a front view showing a display device of an insertion operation detection unit which is used in an endoscope apparatus according to a third embodiment of the present invention.

FIG. 8 shows a display device of an insertion operation detection unit which is used in an endoscope apparatus according to a third embodiment of the present invention. In this embodiment, the invention is applied to a so-called master/slave type endoscope system, which is suited to, for example, the education of endoscopic therapy techniques.

Specifically, in this embodiment, as shown in FIG. 8, the display device 20 is provided with a change-over switch 206 for switching the object of display between a master side and a slave side. By the switching operation of the change-over switch 206, the display device 20 is enabled to display the direction of movement, the insertion amount and the insertion force amount of a master-side or slave-side endoscope insertion section 11. Thereby, the present states of the master side and slave side can alternately be recognized. Therefore, when the invention is applied to the master/slave type endoscope system, the stable, high-precision endoscope insertion operation and endoscopic therapy techniques can be learned both visually and experientially by the switching operation of the change-over switch 206.

The present invention is not limited to the above-described embodiments. Various modifications may be made without departing from the spirit of the invention. For example, even if some structural elements are omitted from all the structural elements disclosed in the embodiments, structures from which these structural elements are omitted may be derived as inventions in the case where the object of the invention and the advantageous effects, which are described in the specification, can be achieved.

What is claimed is:

1. An endoscope apparatus comprising:
an endoscope having an insertion section which is adapted to be inserted into a lumen that is an object of an inspection;
a unit body including:
a substantially cylindrical endoscope guide member with a distal end portion which is adapted to be inserted into the lumen that is the object of the inspection, and an insertion hole in which the insertion section is adapted to be advancibly/retreatably inserted; and
detection means, disposed in the substantially cylindrical endoscope guide member, for detecting a direction of movement, an insertion amount and an insertion force amount of the insertion section in relation to the object of the inspection, which occur in association with an advancement/retreat operation of the insertion section within the insertion hole while the distal end portion is inserted into the lumen; and
display means adapted for displaying the direction of movement, the insertion amount and the insertion force amount of the insertion section, which are detected by the detection means;
wherein:
the substantially cylindrical endoscope guide member includes a proximal end portion,
the insertion hole is adapted for guiding insertion of the insertion section and is formed as an inner cavity of the substantially cylindrical endoscope guide cylindrical member,
the detection means includes an insertion force amount detection section which is provided on the proximal end portion of the substantially cylindrical endoscope guide member, and
the insertion force amount detection section includes:
a plurality of guide rollers disposed around the insertion hole;
base members which are adapted to support the guide rollers;
rotational plates each having one end portion supported on the base member so as to be rotatable about a rotational shaft, and having the other end portion to which the guide roller is rotatably supported so as to be rotatable about a rotational shaft;
a pressure sensor which is disposed to be opposed to the rotational plate on a locus of rotation of the rotational plate, and adapted to detect a pressure due to a contact/separation operation of the rotational plate in interlock with rotation of the rotational plate; and
a control circuit which is adapted to detect an insertion force amount due to an insertion operation of the insertion section, on the basis of a detection signal from the pressure sensor.

2. The endoscope apparatus according to claim 1, wherein the display means is disposed separately from the endoscope.

3. The endoscope apparatus according to claim 1, wherein the display means includes display sections which display a maximum insertion amount, a maximum insertion force amount and a minimum insertion force amount of the insertion section.

4. The endoscope apparatus according to claim 1, wherein the display means includes display sections which display presence/absence of insertion stop, an excessive insertion amount and an excessive insertion force amount of the insertion section.

5. The endoscope apparatus according to claim 1, wherein the display means includes:
a present-state display section which displays the direction of movement, the insertion amount and the insertion force amount of the insertion section, which are detected by the detection means;
a cumulative display section which displays a maximum insertion amount, a maximum insertion force amount and a minimum insertion force amount of the insertion section; and
a condition display section which displays presence/absence of insertion stop, an excessive insertion amount and an excessive insertion force amount of the insertion section.

6. The endoscope apparatus according to claim 1, wherein the display means includes a display-object change-over switch which changes an object of display.

7. The endoscope apparatus according to claim 1, wherein the detection means includes:
a guide roller which guides the insertion section in a direction of advancement/retreat;
an insertion amount detection section which detects the insertion amount of the insertion section; and
an insertion force amount detection section which detects the insertion force amount of the insertion section.

8. The endoscope apparatus according to claim 1, wherein the insertion section has a plurality of magnetic portions which are formed in annular shapes on an outer periphery thereof, the magnetic portions being juxtaposed at predetermined intervals along an axial direction of the insertion section,
the guide cylindrical member includes an insertion amount detection section at an intermediate part thereof,
the insertion amount detection section detects the magnetic portions when the insertion section is inserted in the insertion hole and the insertion section passes by an inside of the insertion amount detection section, and
the control circuit detects the direction of movement and the insertion amount of the insertion section on the basis of a detection signal from the insertion amount detection section.

9. The endoscope apparatus according to claim 8, wherein the insertion amount detection section is composed of a Hall element.

10. The endoscope apparatus according to claim 1, wherein the guide roller has, on a side surface thereof, a plurality of magnetic portions juxtaposed at predetermined intervals along a circumferential direction of a circle centering on the rotational shaft,
the base member is provided with an insertion amount detection section,
the insertion amount detection section detects the magnetic portions on the side surface of the guide roller in accordance with a rotational operation of the guide roller, which occurs due to movement of the insertion section, and
the control circuit detects a rotational angle of the guide roller on the basis of a detection signal from the insertion amount detection section, and detects the direction of movement and the insertion amount of the insertion section.

* * * * *